United States Patent [19]
Osthold et al.

[11] Patent Number: 5,318,508
[45] Date of Patent: Jun. 7, 1994

[54] NAIL CORRECTIVE BRACE

[76] Inventors: Elvira Osthold; Hede Wittmann, both of Walter-Flex-Str. 18, W-8520 Erlangen, Fed. Rep. of Germany

[21] Appl. No.: 919,097

[22] Filed: Jul. 23, 1992

[51] Int. Cl.⁵ .............................................. A61F 5/11
[52] U.S. Cl. ..................................................... 602/31
[58] Field of Search ...................... 602/31, 30, 37, 22, 602/21; 128/81 A, 81 R

[56] References Cited

U.S. PATENT DOCUMENTS

| | | | |
|---|---|---|---|
| 137,106 | 3/1873 | Stedman | 602/31 |
| 884,376 | 4/1908 | Foster | 602/31 |
| 1,785,376 | 12/1930 | Buckner | 602/31 |
| 3,032,032 | 5/1962 | Gifford | 602/31 |
| 5,012,799 | 5/1991 | Remmen | 602/31 |

FOREIGN PATENT DOCUMENTS

| | | | |
|---|---|---|---|
| 3233419 | 3/1984 | Fed. Rep. of Germany | 128/81 A |
| 3711755 | 10/1988 | Fed. Rep. of Germany | 128/81 A |
| 791799 | 3/1958 | United Kingdom | 128/81 A |

*Primary Examiner*—Richard J. Apley
*Assistant Examiner*—Beverly A. Meindl
*Attorney, Agent, or Firm*—Morrison Law Firm

[57] ABSTRACT

A multi-part nail corrective brace for treating an ingrown toe- or fingernail has a brace part and a bridging piece. The brace part has a pair of hooks that are installed under the left and right edges of the nail to be treated. In application, the bridging piece is joined to the brace part by joining loops or indentations. Tension is applied to lever the nail up so that it is no longer ingrown. The joining loops or indentations can be in the form of discs, which can be cut out to enhance their elasticity. These discs may be injection-molded of plastic or rubber.

14 Claims, 4 Drawing Sheets

FIG. 7
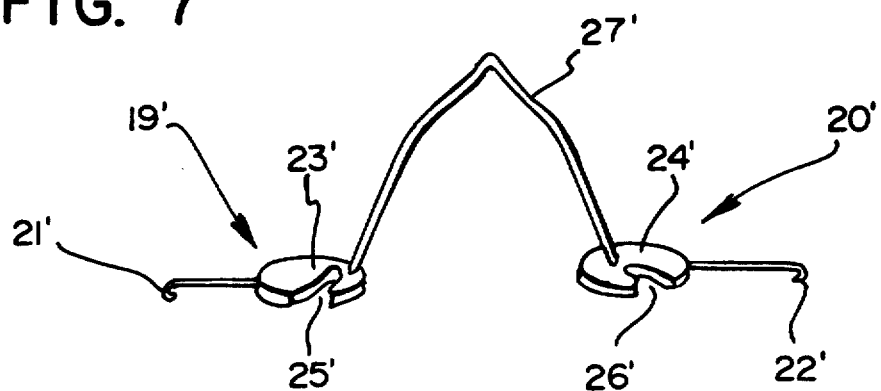
FIG. 8
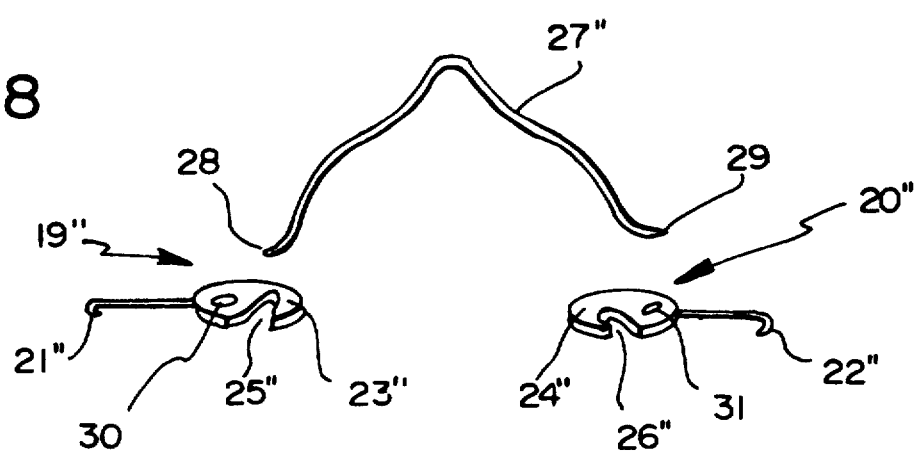
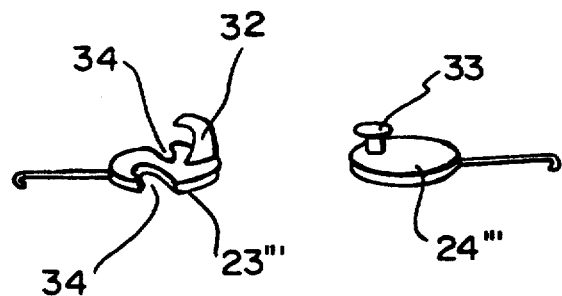
FIG. 9

NAIL CORRECTIVE BRACE

BACKGROUND OF THE INVENTION

This invention relates to a corrective brace for a toe- or fingernail, especially a toenail.

In foot care, toe nails frequently require attention because they become ingrown, that is, their outer edges press painfully into the flesh. Such a condition makes walking difficult. If an ingrown toenail is left untreated, the nail can puncture the skin, leading to an infection that can become serious.

One well-known treatment for an ingrown toenail is surgical removal of the nail. However, the results of this treatment are painful both during and after the operation, and it requires a lengthy period of recuperation. During recuperation it is difficult for the patient to wear socks or stockings and shoes, which in turn makes it impossible to walk normally.

A non-surgical treatment is presented by orthonychia: straightening the nail via a brace. Such a brace, with hooks on the side, grips the nail under the edges and levers them up by spring action. With this action the curvature of the nail is reduced, and the infected area around the ingrown nail heals.

One brace for this treatment is a one-piece or unitary brace. However, a unitary brace is not suitable for treating festering or infected nails. Furthermore, the unitary brace has a disadvantage in that nails vary greatly in their curvature and size.

DE 37 11 755 C2 discloses a nail-correcting brace which has two wire brace parts. It is fixed sideways over the nail and fitted at one end with a hook which is secured under the nail. The other end has a joining indentation to connect the brace with a spring clamp. Even though this brace is better than a unitary brace, it still has a major disadvantage: the spring clamp is not flexible enough for some cases and therefore cannot be used to treat them.

OBJECTS AND SUMMARY OF THE INVENTION

An object of the present invention is to provide a nail corrective brace that overcomes the drawbacks of the prior art.

A further object of the present invention is to provide a multipart nail corrective brace that is flexible and easy to adjust.

Still a further object of the present invention is to provide a multipart nail corrective brace that can be easily fitted to the entire spectrum of nails no matter what their size and curvature.

Still a further object of the present invention is to provide a nail corrective brace that, by force exerted on the side of the nail, lifts it.

Briefly stated, the present invention provides a multipart nail corrective brace for treating an ingrown toe- or fingernail that has a brace part and a bridging piece. The brace part has a pair of hooks that are installed under the left and right edges of the nail to be treated. In application, the bridging piece is joined to the brace part by joining loops or indentations. Tension is applied to lever the nail up so that it is no longer ingrown. The joining loops or indentations can be in the form of discs, which can be cut out to enhance their elasticity.

According to a feature of the invention,

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 7 shows another embodiment of the nail corrective brace of the present invention with joining discs.

FIG. 8 shows still another embodiment of the nail corrective brace of the present invention with joining discs.

FIG. 9 shows special shapes of the joining discs of the nail corrective brace of the present invention.

DETAILED DESCRIPTION OF THE PREFERRED EMBODIMENT

Figure 1:
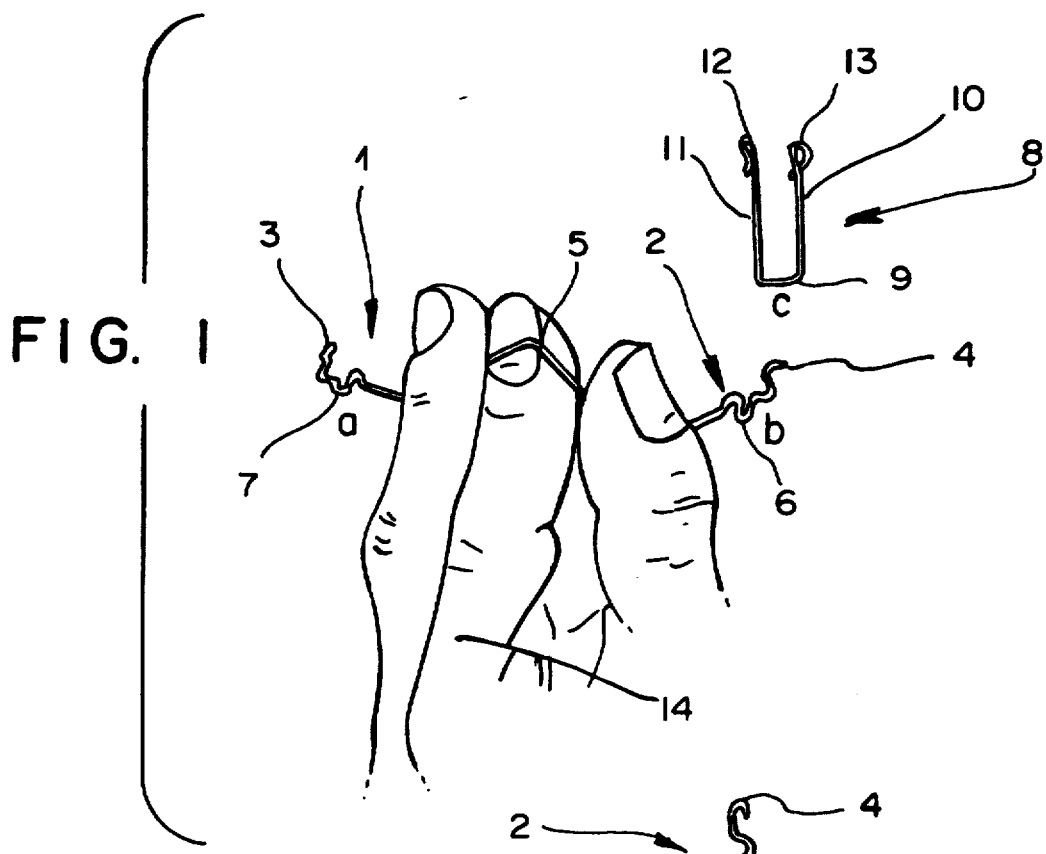
FIG. 1 shows the nail corrective brace of the present invention before application.

Referring to FIG. 1, a nail corrective brace of the present invention has two brace parts 1, 2 and a bridging piece 8. Brace parts 1, 2 are initially formed on the same piece of wire.

A hand 14 is shown gripping a stirrup 5 which is at the center of the piece of wire containing brace parts 1, 2. Brace parts 1, 2 terminate respectively in a pair of hooks 3, 4. The piece of wire containing brace parts 1, 2 also contains, between hooks 3, 4 and stirrup 5, a pair of joining parts, in this embodiment loops 6, 7.

U-shaped bridging piece 8 is used as a connection piece. Bridging piece 8 has a closed end 9 and two free ends 10, 11. Each of free ends 10, 11 has a twisting aid 12, 13. Plastic can be substituted for wire in the fabrication of bridging piece 8.

Figure 2:
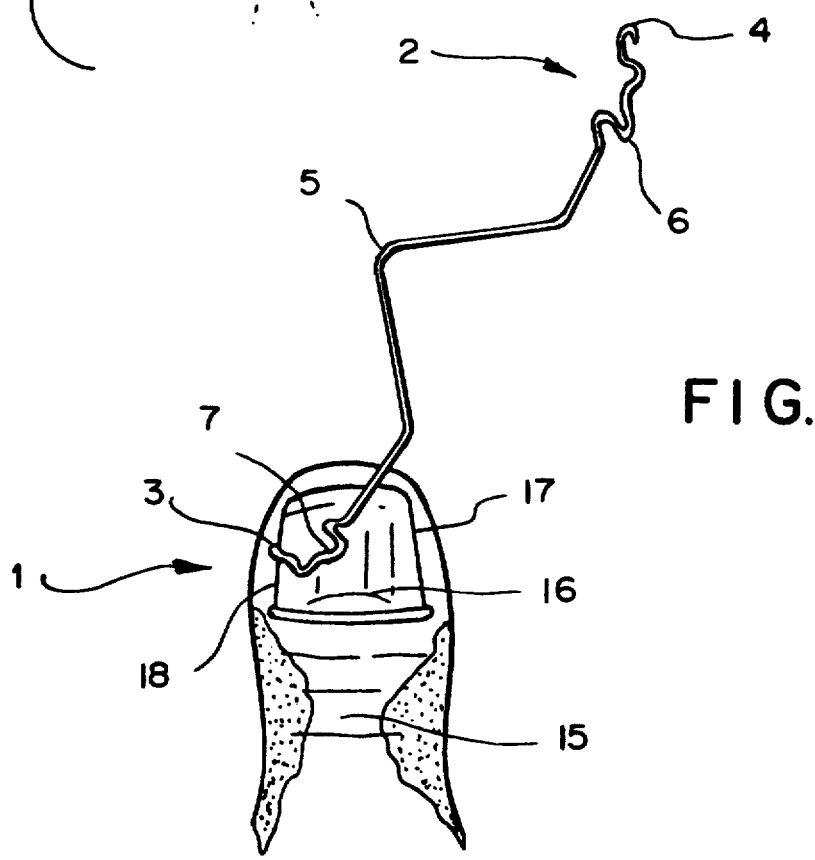
FIG. 2 shows a first step in applying the nail corrective brace of the present invention.
Figure 3:
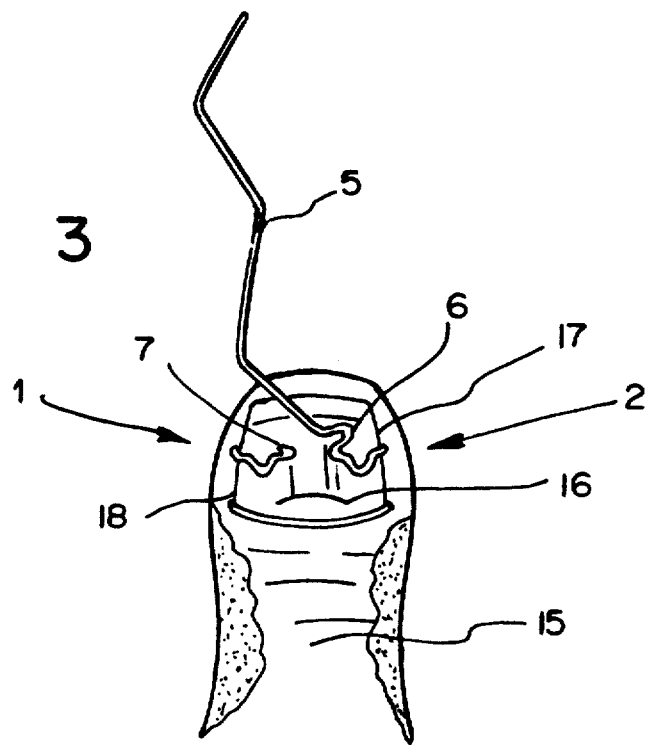
FIG. 3 shows a second step in applying the nail corrective brace of the present invention.
Figure 4:
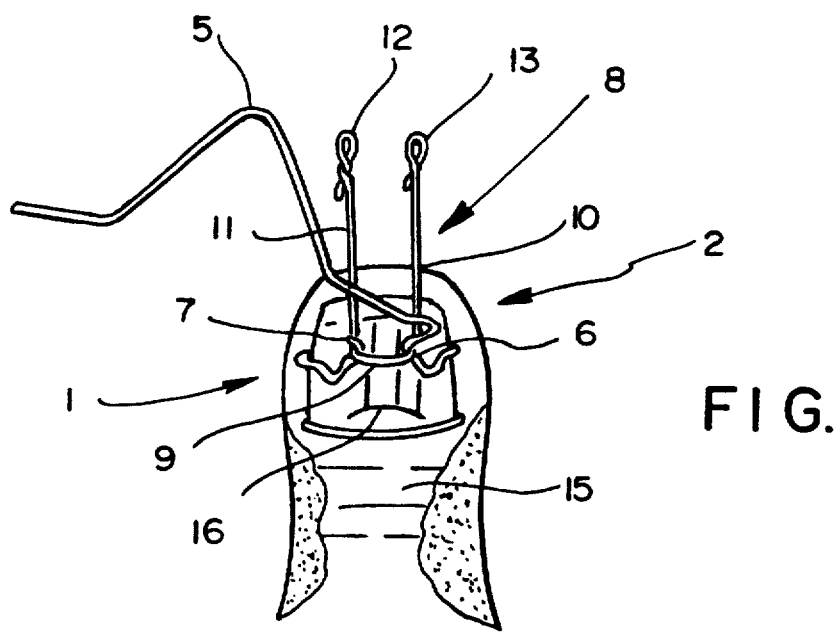
FIG. 4 shows a third step in applying the nail corrective brace of the present invention.

Referring to FIGS. 2–4, the nail corrective brace is applied in a series of steps. Hook 3 is fitted under an edge 18 of a nail 16 of a toe 15. Thereafter the piece of wire containing brace part 1, 2 is severed at the section of stirrup 5 just past loop 7. Then hook 4 of the remaining portion of wire containing brace parts 1, 2 is hooked under an edge 17 of nail 16 of toe 15. Then closed end 9 of bridging piece 8 is hooked into the loops 6, 7, and free ends 10, 11 are then joined with the aid of twisting aids 12, 13. The help of a lever may be required to attain a tension sufficient to lift nail 16. Once nail 16 is braced so that successful treatment can be carried out, the following parts are severed to be as short as possible: loops 6, 7.; free ends 10, 11; and bridging piece 8.

Figure 5:
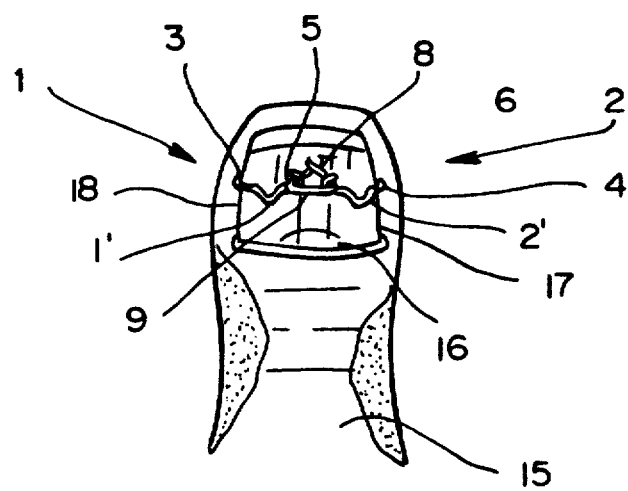
FIG. 5 shows the nail corrective brace of the present invention applied.

Referring to FIG. 5, the nail correcting brace as applied has brace parts 1, 2 grip with hooks 3, 4 under nail edges 17, 18. The two severed portions of brace parts 1, 2 are joined with loops 6, 7, distending brace parts 1 and 2 at crimp sections 1' and 2' respectively to the rest of bridging piece 8. The spring action required to lift nail 16 comes from the joint twisting of the free ends 10, 11, bridging piece 8, and loops 6, 7.

Referring to FIGS. 6–9, in another embodiment, joining parts 19, 19', 19", 20, 20', 20"—two to each application—are discs with indentations rather than loops 6, 7 in the wire containing brace parts 1, 2. Discs 23, 23', 23", 24, 24', 24" having indentations 25, 25', 25", 26, 26', 26" may be employed in any combination. Hooks 21, 21', 21", 22, 22', 22" are wire hooks connected at their straight ends respectively to appropriate discs 23, 23', 23", 24, 24', or 24" by injection molding.

Figure 6:
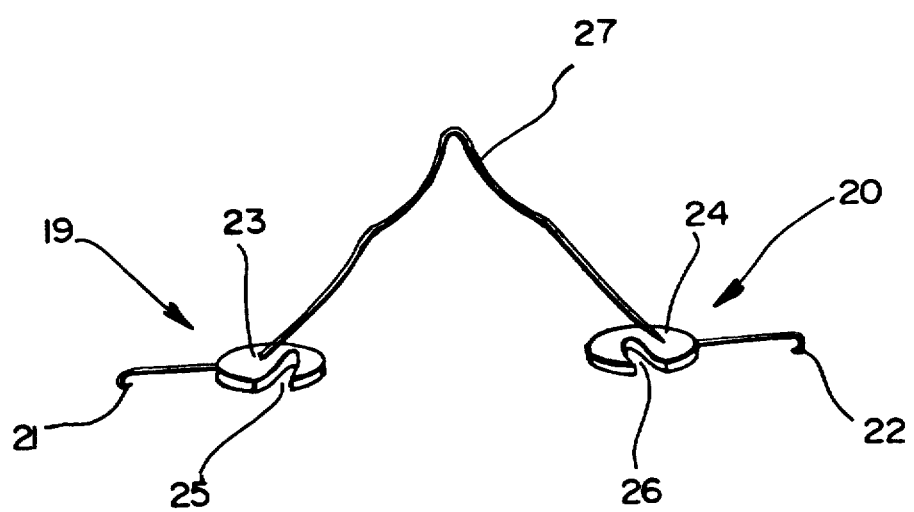
FIG. 6 shows the nail corrective brace of the present invention with joining discs.

FIG. 6 shows a stirrup 27 as the extension or runner of inserted hooks 21, 22 that protrude from discs 25, 26.

FIG. 7 shows a stirrup 27' that is a plastic molding which is directly molded with its ends joined to discs 23' & 24'.

FIG. 8 shows a stirrup 27" of either metal or plastic which can be detachably joined to discs 23" and 24". Two ends 28, 29 of stirrup 27" can be fitted, prior to application of the nail corrective brace, into a pair of guide holes 30, 31 of discs 25", 26", and be removed after application. If detachable stirrup 27" is used, there is no need to sever the wire containing brace parts 1, 2.

Referring to FIGS. 1 to 8, bridging piece 8 and discs 23, 23', 23", 23''', 24, 24', 24", and 24''' can be produced from plastic.

Referring to FIG. 9, in practice it is advantageous to apply tension to the nail in a forward direction and not vertically. Thus discs 23''', 24''' may have a hook 32 or a mushroom-shaped knob 33 to join with wire or plastic bridging piece 8. To increase the flexibility of the discs, which are already somewhat flexible through the use of indentations 25, 25', 25", 26, 26', 26", discs 23''', 24''' can be produced with a plurality of cut outs 34.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A nail corrective brace, comprising:
   at least two brace parts;
   a pair of hooks;
   each of said at least two brace parts terminating at a distal end in a one of said pair of hooks;
   said hooks being effective for lifting a nail;
   a pair of joining parts;
   each of said at least two parts terminating at a proximal end in a one of said pair of joining parts;
   said pair of joining parts being resilient under tension; and
   a twistable bridging piece of sufficient length for uniting said joining parts under tension effected by twisting of said twistable bridging piece about itself, whereby said at least two brace parts flatten said nail so that said nail is not ingrown.

2. A nail corrective brace as in claim 1, wherein said bridging piece is made of wire.

3. A nail corrective brace as in claim 1, wherein said bridging piece is made of plastic.

4. A nail corrective brace as in claim 1, wherein said joining parts are made of wire.

5. A nail corrective brace as in claim 1, wherein said joining parts are made of plastic.

6. A nail corrective brace, comprising:
   at least two brace parts;
   a pair of hooks;
   each of said at least two brace parts terminating at a distal end in one of said pair of hooks;
   said hooks effective for lifting a nail;
   a pair of joining parts;
   each of said at least two brace parts terminating at a proximal end in a one of said pair of joining parts;
   said pair of joining parts being resilient under tension;
   said joining parts being discs; and
   a bridging piece effective for uniting said joining parts under tension, whereby said at least two brace parts flatten said nail so that said nail is not ingrown.

7. A nail corrective brace as in claim 1, wherein said bridging piece has a pair of free ends provided with circular loops for the purpose of facilitating twisting of said twistable bridging piece.

8. A nail corrective brace as in claim 1, wherein said brace parts prior to application of said brace are joined by a stirrup, said stirrup being removed when said brace has been applied.

9. A nail corrective brace as in claim 8, wherein said brace parts are permanently fixed to said stirrup.

10. A nail corrective brace as in claim 8, wherein said brace parts are detachably fixed to said stirrup.

11. A nail corrective brace as in claim 6, wherein said joining parts have top pointing hooks to attach said joining parts to said bridging piece.

12. A nail corrective brace as in claim 6, wherein said joining parts have mushroom-shaped knobs to attach said joining parts to said bridging piece.

13. A nail corrective brace as in claim 6, wherein said discs can each have at least one cut out therein, whereby the elasticity of said discs is enhanced.

14. A nail corrective brace as in claim 1, wherein each of said joining parts include a wire portion having a crimped section for effective a resiliency of said joining parts.

* * * * *